United States Patent
Kwon et al.

(10) Patent No.: US 9,486,490 B2
(45) Date of Patent: Nov. 8, 2016

(54) COMPOSITION FOR PREVENTING OR TREATING CANCER CONTAINING EXTRACTS OF ARTOCARPUS ALTILIS FRUITS, LEAVES, OR STEMS, OR FRACTIONS THEREOF AS ACTIVE INGREDIENTS

(71) Applicant: Korea Research Institute of Bioscience and Biotechnology, Daejeon (KR)

(72) Inventors: Byoung-Mog Kwon, Daejeon (KR); Dong Cho Han, Daejeon (KR); Joongku Lee, Daejeon (KR); Yoon-jeong Jeon, Daejeon (KR); Sang Ho Choi, Daejeon (KR)

(73) Assignee: Korea Research Institute of Bioscience and Biotechnology, Daejeon (KR)

( * ) Notice: Subject to any disclaimer, the term of this patent is extended or adjusted under 35 U.S.C. 154(b) by 1 day.

(21) Appl. No.: 14/398,285

(22) PCT Filed: Jul. 26, 2013

(86) PCT No.: PCT/KR2013/006737
§ 371 (c)(1),
(2) Date: Oct. 31, 2014

(87) PCT Pub. No.: WO2014/035060
PCT Pub. Date: Mar. 6, 2014

(65) Prior Publication Data
US 2015/0125560 A1 May 7, 2015

(30) Foreign Application Priority Data
Aug. 31, 2012 (KR) .................. 10-2012-0096165
Jul. 26, 2013 (KR) .................. 10-2013-0088480

(51) Int. Cl.
*A61K 36/60* (2006.01)
(52) U.S. Cl.
CPC .................................. *A61K 36/60* (2013.01)
(58) Field of Classification Search
CPC ................................................. A61K 36/60
USPC ........................................ 424/777, 774, 779
See application file for complete search history.

(56) References Cited

U.S. PATENT DOCUMENTS

2008/0287374 A1   11/2008   Yamazaki et al.

FOREIGN PATENT DOCUMENTS

KR   10-2009-0109769 A   10/2009
WO        2004075844 A2    9/2004

OTHER PUBLICATIONS

Yu et al. "Geranyl flavonoids fron the leaves of *Artocarpus altilis*" Phytochemistry 68 (2007) 1300-1306.*
Shamaun et al. "Prenylated flavones from *Artocarpus altilis*", Journal National Medical (2010)64:478-481.*
Arung, E. T. et al., "Anti-Cancer Properties of Diethylether Extract of Wood from Sukun (*Artocarpus altilis*) in Human Breast Cancer (T47D) Cells", Tropical Journal of Pharmaceutical Research, Aug. 2009, vol. 8, No. 4, pp. 317-324.
Jagtap, U. B. et al., "Artocarpus: A review of its traditional uses, phytochemistry and pharmacology", Journal of Ethnopharmacology, Apr. 7, 2010, vol. 129, pp. 142-166.
Jain, R. et al., "Screening of in vitro cytotoxic activity of some medicinal plants used traditionally to treat cancer in Chhattisgarh state, India", Asian Pacific Journal of Tropical Biomedicine, Sep. 28, 2011, vol. 1, pp. S147-S150.
Hotta (1989) [Useful Plant Encyclopedia]. 1st Ed. [Heibonsha] (publisher). p. 118.—with English translation.
Mazumdar et al. (Jul. 11, 2011) "Blocking Hedgehog survival signaling at the level of the GLI genes induces DNA damage and extensive cell death in human colon carcinoma cells," Cancer Research. 71(17):5904-5914.
Sanchez et al. (2004) "Inhibition of prostate cancer proliferation by interference with Sonic Hedgehog-GLI1 signaling," Proc. Natl. Acad. Sci. USA. 101(34):12561-12566.
Fang et al. (2008) "Cytotoxic Effects of New Geranyl Chalcone Derivatives Isolated from the Leaves of *Artocarpus communis* in SW 872 Human Liposarcoma Cells," Journal of Agriculture and Food Chemistry. 56(19):8859-8868.
Hsu et al. (Dec. 23, 2010) "Cytotoxic effects of geranyl flavonoid derivatives from the fruit of *Artocarpus communis* in SK-Hep-1 human hepatocellular carcinoma ," Food Chemistry. 127(1):127-134.
Liou et al. (1993) "γ-Pyrone Compounds as Potential Anti-cancer Drugs," Journal of Pharmacy and Pharmacology. 45(9):791-794.
Puspa et al. (2008) "Identification of Cytotoxic Compound from *Artocarpus communis* Leaves Against P-388 Cells," Pakistan Journal of Biological Sciences, 11(21):2517-2520.

* cited by examiner

*Primary Examiner* — Chris R Tate
*Assistant Examiner* — Deborah Davis
(74) *Attorney, Agent, or Firm* — Lathrop & Gage LLP

(57) ABSTRACT

The present invention relates to a pharmaceutical composition for preventing and treating cancer which comprises the extracts of *Artocarpus altilis* fruits, leaves, or stems, or the fractions thereof as active ingredients. The extracts of *Artocarpus altilis* fruits, leaves, or stems, or the fractions thereof, according to the present invention, suppress the activity of signal transducer and activator of transcription3 (STAT3) which plays an important role in the growth of a cancer cell line and in the immune function of the human body, and can thus be effectively used in the prevention and treatment of cancers such as colorectal cancer, stomach cancer, prostate cancer, breast cancer, renal cancer, liver cancer, brain tumor, lung cancer, uterine cancer, colorectal cancer, bladder cancer, or pancreatic cancer.

4 Claims, 3 Drawing Sheets

COMPOSITION FOR PREVENTING OR TREATING CANCER CONTAINING EXTRACTS OF ARTOCARPUS ALTILIS FRUITS, LEAVES, OR STEMS, OR FRACTIONS THEREOF AS ACTIVE INGREDIENTS

This application is a 35 U.S.C. §371 filing of International Application No. PCT/KR2013/006737, filed Jul. 26, 2013, which claims priority to Korean Patent Application No. 10-2013-0088480, filed on Jul. 26, 2013 and Korean Patent Application No. 10-2012-0096165, filed Aug. 31, 2012. The entire contents of each are incorporated herein by reference.

BACKGROUND OF THE INVENTION

1. Field of the Invention

The present invention relates to a composition for preventing and treating cancer which comprises the extracts of *Artocarpus altilis* fruits, leaves, or stems, or the fractions thereof as active ingredients.

2. Description of the Related Art

In spite of the increase of incidence rate of cancer according to the development of human civilization, cancer treatment methods still depend on only surgical operation, radio-therapy and chemo-therapy using about 40 very strong cytotoxic anticancer agents. These treatment methods are only effective in early-stage cancer patients or are limited to specific cancers, so that they cannot hold back the increase of death rate of cancer.

Cancer is the most incurable disease, and the mechanism of cancer development and progress is closely related to other diseases such as vascular diseases, immune diseases, and rheumatism. Based on that conception, various anticancer agents and target mechanisms have been studied. A selective anticancer agent targeting a specific molecule is drawing our attention because it is not only safer and more effective in the treatment but also applicable to tailored medicine and combination therapy.

STAT3 is a transcriptional regulatory factor that regulates the expressions of genes involved in cell growth, differentiation, and apoptosis via intracellular signal transduction in relation to various cytokines and growth factors and also plays a certain role in transforming tumor cells into malignant cancer cells by over-expression and abnormal activation. The activation of STAT3 is triggered by the recognition of extracellular cytokines or growth factors (for example, EGF, PDGF, and IL-6, etc) by receptor proteins or by the phosphorylation by cancer inducing proteins such as Src or Ras, etc.

To activate STAT3, it is necessary the phosphorylation of tyrosine 705 by non-receptor proteins that usually phosphorylate the receptor proteins or tyrosine. The representative proteins that can phosphorylate tyrosine 705 of STAT3 are epidermal growth factor receptor (EGFR), Src, Janus activated kinase (JAK) activating enzyme, and extracellular signal-regulated kinase (ERK), etc.

As stated before, STAT is a signal transduction and transcriptional regulatory protein and is activated by the extracellular stimuli such as cytokines, hormones, and growth factors to lead the phosphorylation of tyrosine residue, during which it turns into dimer via the interaction with SH2 domain and then migrates into the nucleus to bind with a specific promoter. The STAT in the nucleus accelerates the expressions of cycline D and survivin, which play an important role in cancer cell growth, and also induces the expressions of Bcl-xL, Bcl-2, and Mcl-1, which suppress cancer cell apoptosis. STAT also accelerates the expression of VEGF playing an important role in cancer metastasis. The signal system of STAT can be stopped by dephosphorylation and protein degradation.

Active forms of three types of STAT proteins, STAT1, STAT3, and STAT5, are found in various cancers. In particular, STAT3 is activated not only in blood tumors including leukaemia but also in solid tumors such as breast cancer, head and neck cancer, melanoma, ovarian cancer, lung cancer, pancreatic cancer, and prostate cancer, suggesting that it can be an important target of cancer treatment (Hua Yu and Richard Jove, *Nature Review Cancer* (2004), 8, 945).

TABLE 1

| Tumor types | (Activated STAT |
|---|---|
| Blood tumors | |
| Multiple myeloma | STAT1, STAT3 |
| Leukaemias | |
| HTLV-I-dependent | STAT3, STAT5 |
| Erythroleukaemia | STAT1, STAT5 |
| Acute myelogenous leukaemia (AML) | STAT1, STAT3, STAT5 |
| Chronic myelogenous leukaemia (CML) | STAT5 |
| Large granular lymphocyte leukaemia (LGL) | STAT3 |
| Lymphomas | STAT3 |
| Non-Hodgkins lymphoma (NHL) | STAT3 |
| Mycosis fungoides | STAT3 |
| Cutaneous T-cell lymphoma | STAT3 |
| Anaplastic large-cell lymphoma (ALCL) | STAT3 |
| Solid tumors | |
| Breast cancer | STAT1, STAT3, STAT5 |
| Head and neck cancer | STAT1, STAT3, STAT5 |
| Melanoma | STAT3 |
| Ovarian cancer | STAT3 |
| Lung cancer | STAT3 |
| Pancreatic cancer | STAT3 |
| Prostate cancer | STAT3 |

Suppression of the activity of STAT3 thus is an important core technology in the development of effective and practical anticancer agents using the combination of anticancer mechanisms such as apoptosis induction (Catlett-Falcone R. et al., *Immunity* (1999), 10, 105), angiogenesis suppression (Niu, G. et al., *Oncogene* (2002), 21, 2000), and immune evasion blockage (Wang T. et al., *Nature Medicine* (2004), 10, 48). Therefore, greater therapeutic effect than what the conventional anticancer agent characterized by monologic action can be expected. STAT protein is not only involved in tumor related mechanisms but also involved in various other intracellular functions. So, the development of STAT inhibitor can be an important core technology for the development of immune inhibitors and even anti-diabetic agents. Major immune related functions of STAT have been disclosed by the experiment with a specific gene knock-out mouse. Related target genes have also been informed, which are as follows (Nature Review Cancer 9, 798, 2009).

TABLE 2

| STAT | Key activators | Main target genes | Example genes |
|---|---|---|---|
| STAT1 | IFN, IFNa and IFNβ | TH1-type immunostimulatory and pro-apoptosis | TBX21, CD80, CD40, IL-12, CDKN1A and some caspases |
| STAT2 | IFNa and IFNβ | TH1-type Immunostimulatory and pro-apoptosis | CD80 and CD40 |

TABLE 2-continued

| STAT | Key activators | Main target genes | Example genes |
|---|---|---|---|
| STAT3 | IL-6, IL-10, IL-23, IL-21, IL-11, LIF and OSM | TH17-type, anti-apoptosis, pro-proliferation, and metastasis | IL-17, IL-23, BCL-XL, BCL-2, MCL1, CCND1 and VEGF |
| STAT4 | IL-12 | TH1-type, especially IFN | IFN |
| STAT5 | IL-2, GM-CSF, | Anti-apoptosis, | BCL-XL, CCND2 |
| STAT5B | IL-15, IL-7, IL-3, IL-5, growth hormones and prolactin | pro-proliferation and differentiation | and FOXP3 |
| STAT6 | IL-4 and IL-13 | TH2-type, and anti-apoptosis | GATA3 and BCL-2 |

Researchers at Columbia University reported their study as "STAT3 reprograms neural stem cells along the aberrant mesenchymal lineage" (Nature 463, 318, 2010). STAT3 is one of the small genes involved in the proliferation of cancer stem cells, which means the gene regulates 6 typical functions of cancer, that are growth, metastasis, angiogenesis, apoptosis evasion, tissue penetration, and cell immortalization. It has been known that cancer stem cells are involved in cancer metastasis, treatment resistance, and recurrence. Therefore, recent study for the development of an anticancer agent is mainly targeting cancer stem cells.

The scientific name of breadfruit tree is *Artocarpus altilis* (Parkinson) Fosberg, and this tree has been used as a traditional folk medicine in Southeast Asia and Africa to treat sore eyes and sciatica. This natural medicine is recently tried to treat malaria or dengue fever as well. So, it can be said that breadfruit tree is being used to treat sore eyes and sciatica and is confirmed to be effective in treating malaria, yellow fever, and dengue fever, and is even used to treat liver cirrhosis, hypertension, and diabetes particularly in Indonesia (J. Agric. Food Chem. 60, 3867, 2012; Phytotherapy Res. 20, 1052, 2006).

The present inventors screened resources that could regulate the activity of STAT3 from various traditional natural medicines and afterward reported the result saying that cryptotanshinone of *Salvia miltiorrhiza* could regulate the phosphorylation of STAT to bring anticancer effect (Cryptotanshinone Inhibits Constitutive Signal Transducer and Activator of Transcription 3 Function through Blocking the Dimerization in DU145 Prostate Cancer Cells, Cancer Research 69, 193, 2009).

The present inventors have screened resources that could regulate the activity of STAT3 from natural materials. As a result, the inventors completed this invention by confirming that the extract of *Artocarpus altilis* or the fractions thereof could efficiently suppress the activity of STAT3 involved in the abnormal activity or over-expression in cancer cell lines of rectal cancer, prostate cancer, breast cancer, and colorectal cancer, with exhibiting the cancer cell growth inhibition effect, so that it could be effectively used in the treatment of diseases attributed to STAT3 activity and cancer.

SUMMARY OF THE INVENTION

It is an object of the present invention to provide a pharmaceutical composition for the prevention and treatment of cancer or a health functional food for the prevention and improvement of cancer which comprises the extracts of *Artocarpus altilis* fruits, leaves, or stems, or the fractions thereof as active ingredients.

To achieve the above object, the present invention provides a pharmaceutical composition for the prevention and treatment of cancer comprising the extracts of *Artocarpus altilis* fruits, leaves, or stems, or the fractions thereof as active ingredients.

The present invention also provides a health functional food composition for the prevention and improvement of cancer comprising the extracts of *Artocarpus altilis* fruits, leaves, or stems, or the fractions thereof as active ingredients.

The present invention also provides a method for treating cancer thereof which includes the step of administering a pharmaceutically effective dose of *Artocarpus altilis* fruits, leaves, or stems extract to a subject having cancer thereof.

The present invention also provides a method for treating cancer thereof which includes the step of administering a pharmaceutically effective dose of *Artocarpus altilis* fruits, leaves, or stems extract of fraction to a subject having cancer thereof.

The present invention also provides a method for preventing cancer thereof which includes the step of administering a pharmaceutically effective dose of *Artocarpus altilis* fruits, leaves, or stems extract to a subject.

The present invention also provides a method for preventing cancer thereof which includes the step of administering a pharmaceutically effective dose of *Artocarpus altilis* fruits, leaves, or stems extract of fraction to a subject.

The present invention also provides a use of the extract of *Artocarpus altilis* fruits, leaves, or stems as an active ingredient of pharmaceutical composition for preventing and treating cancer thereof.

The present invention also provides a use of the fraction of *Artocarpus altilis* fruits, leaves, or stems extract as an active ingredient of pharmaceutical composition for preventing and treating cancer thereof.

The present invention also provides a use of the extract of *Artocarpus altilis* fruits, leaves, or stems as an active ingredient of health food composition for preventing and improving cancer thereof.

The present invention also provides a use of the fraction of *Artocarpus altilis* fruits, leaves, or stems extract as an active ingredient of health food composition for preventing and improving cancer thereof.

Advantageous Effect

The extracts of *Artocarpus altilis* fruits, leaves, or stems, or the fractions thereof can efficiently suppress the activity of STAT3 involved in the over-expression and aberrant activity in cancer cell lines of rectal cancer, prostate cancer, breast cancer, and colorectal cancer, confirming cancer cell growth inhibition effect, so that they can be effectively used for a composition for preventing or treating cancer and for a health functional food for preventing and improving cancer.

BRIEF DESCRIPTION OF THE DRAWINGS

The application of the preferred embodiments of the present invention is best understood with reference to the accompanying drawings, wherein.

DESCRIPTION OF THE PREFERRED EMBODIMENTS

Figure 1:
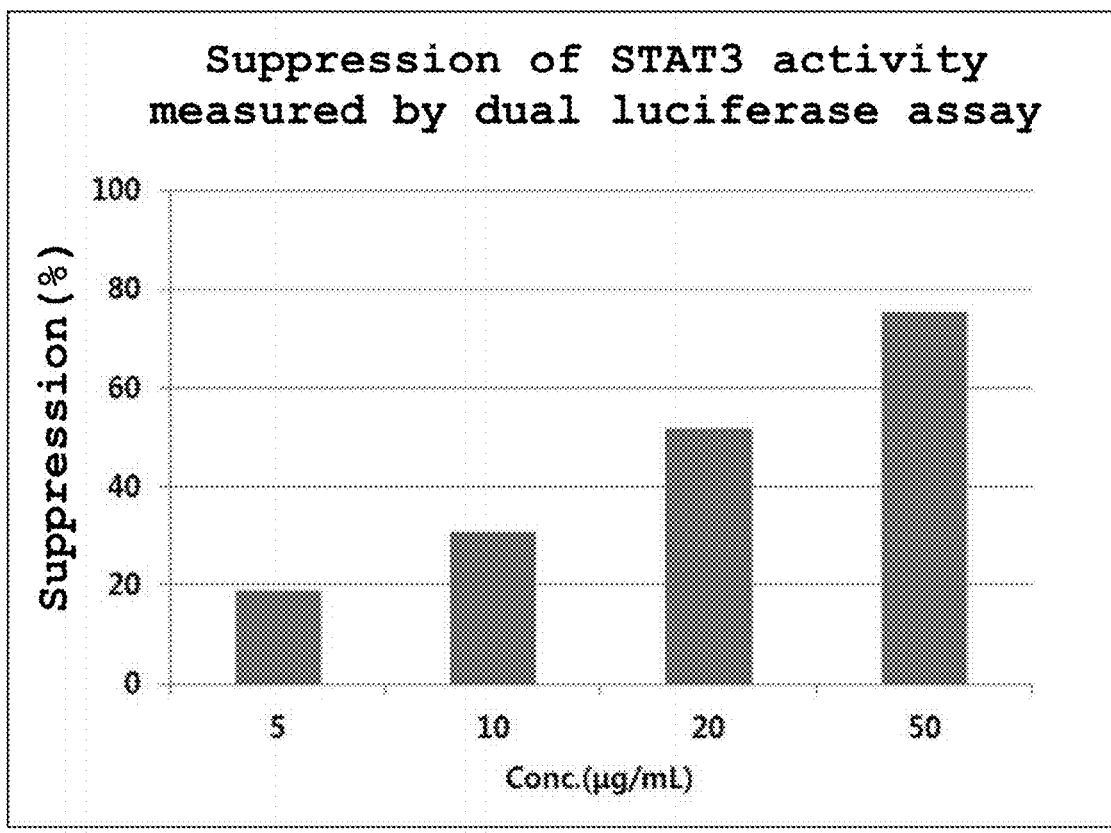
FIG. 1 is a diagram illustrating the suppression of STAT3 activity in a rectal cancer cell line (HCT116) treated with the extracts of *Artocarpus altilis* fruits, leaves, or stems, measured by dual *luciferase* assay.

Hereinafter, the terms used in this invention are described.

The term "anticancer" used in this invention indicates the suppression of cancer cell formation or proliferation, or the action or function to inhibit or block the killing ability of cancer cells. This term further means the prevention and treatment of cancer.

The term "prevention" or "preventing" used in this invention indicates every activity that possibly inhibits the tumor formation or delays the out-break by administering the composition of the present invention.

The term "treatment" or "treating" and "improvement" or "improving" used in this invention indicate all the activity that can improve symptoms of the said disease or change them favorably by administering the composition of the present invention.

The term "administration" or "administering" used in this invention indicates the action of providing a certain amount of the composition of the present invention to a patient via a random but proper method.

The term "patient" used in this invention indicates human and any animals including monkey, dog, goat, pig, and rat which have the disease that can be improved by the administration of the composition of the present invention.

The term "pharmaceutically effective dose" used in this invention indicates the amount enough to treat disease, more precisely a medically reasonable and applicable amount or acceptable risky amount of the composition, which can be determined by considering type and severity of disease, drug activity, drug sensitivity, administration time, administration pathway, excretion, treatment period, other drugs co-treated, and other factors considered by those in the art in this field.

Hereinafter, the present invention is described in detail.

The present invention provides a pharmaceutical composition for the prevention and treatment of cancer comprising the extracts of *Artocarpus altilis* fruits, leaves, or stems as active ingredients.

The said extract can be extracted by using water, $C_1$~$C_2$ lower alcohol or the mixed solvent thereof, but not always limited thereto.

The lower alcohol is preferably ethanol or methanol, but not always limited thereto.

The extracts of *Artocarpus altilis* fruits, leaves, or stems can be prepared by the preparation method composed of the following steps, but not always limited thereto:

1) adding an extraction solvent to *Artocarpus altilis*, followed by extraction;
2) cooling the extract obtained in step 1) and filtering thereof; and
3) concentrating the extract filtered in step 2) under reduced pressure and drying thereof.

In the above method, the *Artocarpus altilis* of step 1) can be cultivated or purchased. The said *Artocarpus altilis* indicates the fruits, leaves, or stems of the tree, but not always limited thereto.

The method for the extraction of *Artocarpus altilis* fruits, leaves, or stems can be one of the conventional methods well known to those in the art, such as filtration, hot-water extraction, soaking extraction, reflux cold extraction, and ultrasonification extraction, but is preferably hot-water extraction with 1~5 repeats, and more preferably with 3 repeats, but not always limited thereto. The volume of the extraction solvent is preferably 0.1~10 times the dry weight of *Artocarpus altilis*, and more preferably 0.3~5 times the dry weight, but not always limited thereto. The extraction temperature is preferably 20° C.~40° C., but not always limited thereto. The extraction time is preferably 12~48 hours, but not always limited thereto.

In the above method, the concentration under reduced pressure in step 3) is performed by using vacuum concentrator or rotary evaporator, but not always limited thereto. In the above method, the drying process is preferably performed by low pressure drying, vacuum drying, boiling drying, spray drying, or freeze drying, but not always limited thereto.

The extracts of *Artocarpus altilis* fruits, leaves, or stems of the present invention are supposed to suppress the activity of STAT3 (signal transducers and activators of transcription 3), but not always limited thereto.

The cancer herein can be selected from the group consisting of colorectal cancer, stomach cancer, prostate cancer, breast cancer, renal cancer, liver cancer, brain tumor, lung cancer, uterine cancer, colon cancer, bladder cancer, and pancreatic cancer, but not always limited thereto.

The present invention also includes the active fractions of the extracts of *Artocarpus altilis* fruits, leaves, or stems obtained by partially purifying the extracts with 50%-100% methanol as active ingredients, but not always limited thereto.

The extracts of the present invention are supposed to suppress the activity of STAT3, but not always limited thereto.

The cancer herein can be selected from the group consisting of colorectal cancer, stomach cancer, prostate cancer, breast cancer, renal cancer, liver cancer, brain tumor, lung cancer, uterine cancer, colon cancer, bladder cancer, and pancreatic cancer, but not always limited thereto.

The anticancer effect of the extracts of *Artocarpus altilis* fruits, leaves, or stems of the present invention is a novel use that has never been disclosed before. The present inventors performed WST-1 test with human cancer cell lines including prostate cancer, breast cancer, pancreatic cancer, lung cancer, etc, to prove the effect of the extracts. As a result, the extracts exhibited 50% growth inhibition effect ($GI_{50}$) in those cancer cell lines at the concentrations of 30~50 ug/ml. In particular, when a prostate cancer cell line was treated with the extracts of *Artocarpus altilis* leaves or stems, or specific fractions thereof, phosphorylation of STAT3 was suppressed (see FIG. 1).

Figure 2:
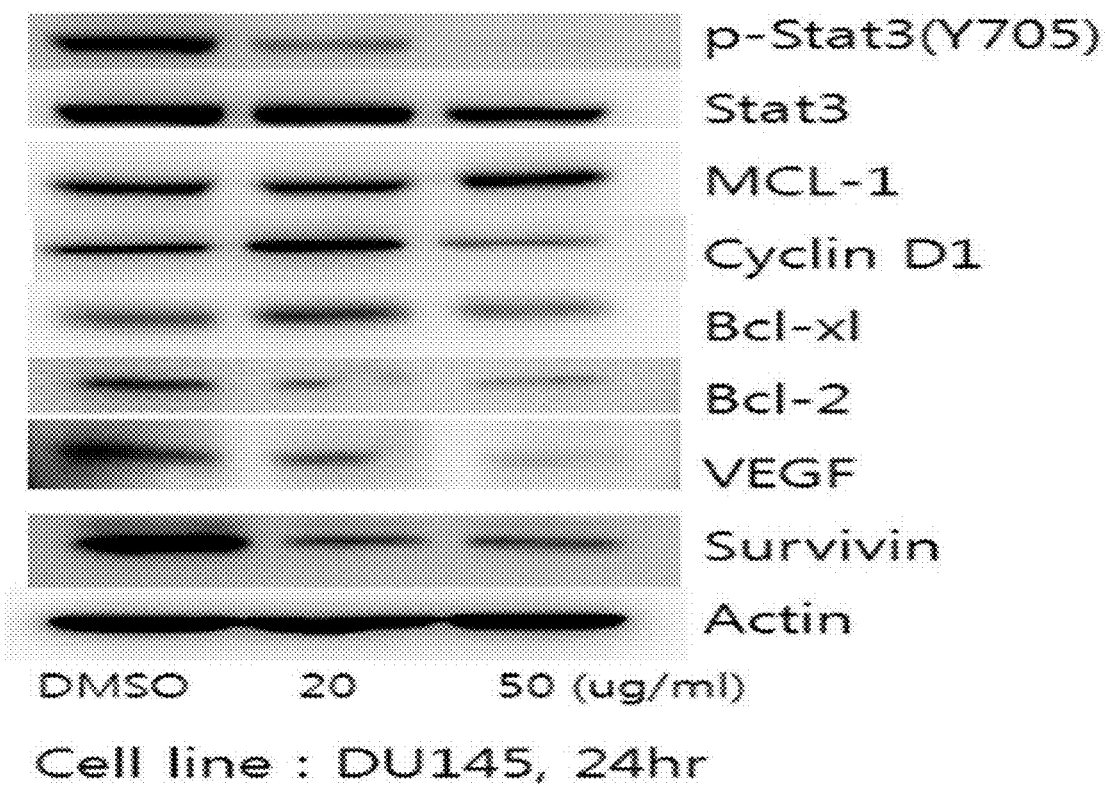
FIG. 2 is a diagram illustrating the suppression of STAT3 activity in a prostate cancer cell line (DU145) treated with the extracts of *Artocarpus altilis* fruits, leaves, or stems, and the expressions of target proteins cyclin D1, BCL-XL, BCL-2, VEGF, MCL-1, and survivin therein.

The specific fractions obtained from the extracts of *Artocarpus altilis* fruits, leaves, or stems could suppress phosphorylation of STAT3, resulting in the inhibition of the expressions of STAT3 related target molecules, cyclin D1, Bcl-xl, Bcl-2, VEGF, and survivin (see FIG. 2).

The extracts of *Artocarpus altilis* fruits, leaves, or stems of the present invention are supposed to suppress the activity of STAT3, but not always limited thereto.

To investigate whether or not the extracts of *Artocarpus altilis* fruits, leaves, or stems or the active fractions thereof could suppress the activity of STAT3, the rectal cancer cell line HCT116 was transfected with the plasmid characteristically increasing the expression of firefly *luciferase* in proportion to the activity of STAT3 and also transfected with the plasmid expressing *Renilla luciferase* regardless of the activity of STAT3. Then, the activity of STAT3 was measured. As a result, the extracts of *Artocarpus altilis* fruits, leaves, or stems suppressed the activity of STAT3 by 50% at the concentration of 50 ug/mL and the active fractions obtained from those extracts suppressed the activity of STAT3 by 75% at the concentration of 50 ug/mL.

To investigate whether or not the extracts of *Artocarpus altilis* fruits, leaves, or stems, and the active fractions thereof could suppress the activity of STAT3, the prostate cancer cell line DU145 was treated with 20 ug/mL and 50 ug/mL of the active fractions of *Artocarpus altilis* fruits, leaves, or stems, followed by Western blotting to measure the activity of STAT3.

The target proteins of STAT3, cyclin D1, Bcl-xl, Bcl-2, VEGF, and survivin, were also treated with 20 ug/mL and 50 ug/mL of the active fractions of *Artocarpus altilis* fruits, leaves, or stems, followed by western blotting to measure the activity of STAT3. As a result, the active fractions of *Artocarpus altilis* of the present invention suppressed the activity of STAT3 not only in the prostate cancer cell line DU145 but also in the STAT3 target proteins cycline D1, Bcl-xl, Bcl-2, VEGF, and survivin at the concentrations of 20 ug/mL and 50 ug/mL. Particularly, the active fractions suppressed the activity of STAT3 more strongly at the concentration of 50 ug/mL.

To investigate whether or not the extracts of *Artocarpus altilis* fruits, leaves, or stems or the active fractions thereof could inhibit the growth of tumor in prostate cancer and could reduce the volume of the tumor, the extracts and the fractions were treated to the test mouse. As a result, the fractions of *Artocarpus altilis* inhibited the tumor growth by 35.0% (<0.05) in the group treated with 30 mg/kg of the fractions. The tumor DU-145 was taken and weighed. As a result, the weight of the tumor was reduced significantly in the group treated with the fractions of *Artocarpus altilis* by 42.3% (<0.05) (see FIG. 3).

Therefore, it was confirmed that the extracts of *Artocarpus altilis* fruits, leaves, or stems, or the fractions thereof of the present invention could efficiently suppress the activity of STAT3 so as to inhibit the growth of cancer, so that they could be effectively used as a pharmaceutical composition for the prevention and treatment of cancer.

The composition for the prevention and treatment of cancer of the present invention can contain the extracts of *Artocarpus altilis*, the fractions thereof and the mixture thereof, and additionally one or more active ingredients having the same or similar functions to the above.

The extracts of *Artocarpus altilis* fruits, leaves, or stems, the fractions thereof and the mixture thereof of the present invention can be administered orally or parenterally and be used in general forms of pharmaceutical formulation. That is, the composition of the present invention can be prepared for oral or parenteral administration by mixing with generally used diluents or excipients such as fillers, extenders, binders, wetting agents, disintegrating agents and surfactants. Solid formulations for oral administration are tablets, pills, powders, granules and capsules. These solid formulations are prepared by mixing the pharmaceutical composition of the present invention with one or more suitable excipients such as starch, calcium carbonate, sucrose or lactose, gelatin, etc. Except for the simple excipients, lubricants, for example magnesium stearate, talc, etc, can be used. Liquid formulations for oral administrations are suspensions, solutions, emulsions and syrups, and the above-mentioned formulations can contain various excipients such as wetting agents, sweeteners, aromatics and preservatives in addition to generally used simple diluents such as water and liquid paraffin. Formulations for parenteral administration are sterilized aqueous solutions, water-insoluble excipients, suspensions, emulsions, lyophilized preparations and suppositories. Water insoluble excipients and suspensions can contain, in addition to the active compound or compounds, propylene glycol, polyethylene glycol, vegetable oil like olive oil, injectable ester like ethylolate, etc. Suppositories can contain, in addition to the active compound or compounds, witepsol, macrogol, tween 61, cacao butter, laurin butter, glycerol, gelatin, etc. The composition of the present invention can be administered by parenterally and the parenteral administration includes subcutaneous injection, intravenous injection, and intramuscular injection.

The dosage unit can contain, for example, 1, 2, 3 or 4 individual doses or ½, ⅓ or ¼ of an individual dose. An individual dose preferably contains the amount of active compound which is administered in one application and which usually corresponds to a whole, ½, ⅓ or ¼ of a daily dose. Effective dosage of the composition of the present invention is 0.01~10 g/kg, and preferably 0.1 g~5 g/kg, and administration frequency is preferably 1~6 times a day. However, the dosage can be adjusted by considering various factors such as administration pathway, severity of disease, patient's gender, weight, and age, etc. Therefore, the preferable dosage cannot limit the scope of the invention in any way.

The composition of the present invention is evaluated to be a safe substance since its estimated $LD_{50}$ value is much greater than 1 g/kg in rats, which is confirmed by toxicity assay with rats tested via oral administration. The composition of the present invention can be administered alone or treated together with surgical operation, hormone therapy, chemo-therapy and biological regulators to prevent and treat cancer.

The present invention also provides a health functional food composition for the prevention and improvement of cancer which comprises the extracts of *Artocarpus altilis* fruits, leaves, or stems as active ingredients.

The present invention also provides a health functional food composition for the prevention and improvement of cancer which comprises the fractions of *Artocarpus altilis* fruits, leaves, or stems as active ingredients.

The said extract can be extracted by using water, $C_1$~$C_2$ lower alcohol or the mixed solvent thereof, but not always limited thereto.

The lower alcohol is preferably ethanol or methanol, but not always limited thereto.

The extracts of *Artocarpus altilis* fruits, leaves, or stems can be prepared by the preparation method composed of the following steps, but not always limited thereto:

1) adding an extraction solvent to *Artocarpus altilis*, followed by extraction;

2) cooling the extract obtained in step 1) and filtering thereof; and 3) concentrating the extract filtered in step 2) under reduced pressure and drying thereof.

In the above method, the *Artocarpus altilis* of step 1) can be cultivated or purchased. The said *Artocarpus altilis* indicates the fruits, leaves, or stems of the tree, but not always limited thereto.

The method for the extraction of *Artocarpus altilis* fruits, leaves, or stems can be one of the conventional methods well known to those in the art, such as filtration, hot-water extraction, soaking extraction, reflux cold extraction, and ultrasonification extraction, but is preferably hot-water extraction with 1~5 repeats, and more preferably with 3 repeats, but not always limited thereto. The volume of the extraction solvent is preferably 0.1~10 times the dry weight of *Artocarpus altilis*, and more preferably 0.3~5 times the dry weight, but not always limited thereto. The extraction temperature is preferably 20° C.~40° C., but not always limited thereto. The extraction time is preferably 12~48 hours, but not always limited thereto.

In the above method, the concentration under reduced pressure in step 3) is performed by using vacuum concentrator or rotary evaporator, but not always limited thereto. In the above method, the drying process is preferably performed by low pressure drying, vacuum drying, boiling drying, spray drying, or freeze drying, but not always limited thereto.

The extracts of *Artocarpus altilis* fruits, leaves, or stems of the present invention are supposed to suppress the activity of STAT3, but not always limited thereto.

The cancer herein can be selected from the group consisting of colorectal cancer, stomach cancer, prostate cancer, breast cancer, renal cancer, liver cancer, brain tumor, lung cancer, uterine cancer, colon cancer, bladder cancer, and pancreatic cancer, but not always limited thereto.

The present invention also includes the active fractions of the extracts of *Artocarpus altilis* fruits, leaves, or stems obtained by additionally purifying the extracts with 50%~100% methanol as active ingredients, but not always limited thereto.

The fractions of *Artocarpus altilis* fruits, leaves, or stems of the present invention are supposed to suppress the activity of STAT3 (signal transducers and activators of transcription 3), but not always limited thereto.

The cancer herein can be selected from the group consisting of colorectal cancer, stomach cancer, prostate cancer, breast cancer, renal cancer, liver cancer, brain tumor, lung cancer, uterine cancer, colon cancer, bladder cancer, and pancreatic cancer, but not always limited thereto.

When the extracts of *Artocarpus altilis* fruits, leaves, or stems, the fractions thereof, or the mixture thereof of the present invention are used as food additives, the said extracts, the fractions, or the mixture can be used as they are or mixed with other food components according to the conventional method. The extraction of *Artocarpus altilis* fruits, leaves, or stems is preferably performed by using hot-water and ethanol, and at this time the preferable concentration of ethanol is 50~100%. The mixing ratio of active ingredients can be regulated according to the purpose of use (prevention, health enhancement or treatment). In general, to produce health food or beverages, the composition of the present invention is added preferably by up to 15 weight part and more preferably by up to 10 weight part. However, if long term administration is required for health and hygiene or regulating health condition, the content can be lower than the above but higher content can be accepted as well since the composition of the present invention has been proved to be very safe.

The food herein is not limited. For example, the extracts of *Artocarpus altilis* fruits, leaves, or stems, the active fractions thereof, or the mixture thereof of the present invention can be added to meats, sausages, breads, chocolates, candies, snacks, cookies, pizza, ramyuns, flour products, gums, dairy products including ice cream, soups, beverages, tea, drinks, alcohol drinks and vitamin complex, etc, and in wide sense, almost every food applicable in the production of health food can be included.

The composition for health beverages of the present invention can additionally include various flavors or natural carbohydrates, etc, like other beverages. The natural carbohydrates above can be one of monosaccharides such as glucose and fructose, disaccharides such as maltose and sucrose, polysaccharides such as dextrin and cyclodextrin, and glucose alcohols such as xilytole, sorbitol and erythritol. Besides, natural sweetening agents such as thaumatin and stevia extract, and synthetic sweetening agents such as saccharin and aspartame can be included as a sweetening agent. The content of the natural carbohydrate is preferably 0.01~0.04 g and more preferably 0.02~0.03 g in 100 ml of the composition.

In addition to the ingredients mentioned above, the extracts of *Artocarpus altilis* fruits, leaves, or stems, the active fractions thereof, or the mixture thereof of the present invention can include in variety of nutrients, vitamins, minerals, flavors, coloring agents, pectic acid and its salts, alginic acid and its salts, organic acid, protective colloidal viscosifiers, pH regulators, stabilizers, antiseptics, glycerin, alcohols, carbonators which used to be added to soda, etc. The extracts of *Artocarpus altilis* fruits, leaves, or stems, the active fractions thereof, or the mixture thereof of the present invention can also include fruit flesh addable to natural fruit juice, fruit beverages and vegetable beverages. All the mentioned ingredients can be added singly or together.

The present invention also provides a method for treating cancer thereof which includes the step of administering a pharmaceutically effective dose of *Artocarpus altilis* fruits, leaves, or stems extracts to a subject having cancer thereof.

The present invention also provides a method for treating cancer thereof which includes the step of administering a pharmaceutically effective dose of *Artocarpus altilis* fruits, leaves, or stems fractions of the extracts to a subject having cancer thereof.

The present invention also provides a method for preventing cancer thereof which includes the step of administering a pharmaceutically effective dose of *Artocarpus altilis* fruits, leaves, or stems extracts to a subject.

The present invention also provides a method for preventing cancer thereof which includes the step of administering a pharmaceutically effective dose of *Artocarpus altilis* fruits, leaves, or stems fractions of the extracts to a subject.

The pharmaceutically effective dose herein is 0.0001~100 mg/kg per day and preferably 0.001~10 mg/kg per day, but not always limited thereto. The effective dose can be determined according to weight, age, gender, health condition, diet, administration frequency, administration method, excretion and severity of disease.

The composition of the present invention can be administered orally or parenterally, and the parenteral administration includes intraperitoneal injection, intrarectal injection, subcutaneous injection, intravenous injection, intramuscular injection, intrauterine injection, and intracerebroventricular injection.

The present invention extracts of *Artocarpus altilis* fruits, leaves, or stems, or the fractions thereof of the present invention could efficiently suppress the activity of STAT3 so as to inhibit the growth of cancer, so that The present invention extracts of *Artocarpus altilis* fruits, leaves, or stems, or the fractions as active ingredients of pharmaceutical composition for the treatment.

The present invention also provides a use of the extracts of *Artocarpus altilis* fruits, leaves, or stems as an active ingredient of pharmaceutical composition for preventing and treating cancer thereof.

The present invention also provides a use of the fractions of *Artocarpus altilis* fruits, leaves, or stems extracts as an active ingredient of pharmaceutical composition for preventing and treating cancer thereof.

The present invention extracts of *Artocarpus altilis* fruits, leaves, or stems, or the fractions thereof of the present invention could efficiently suppress the activity of STAT3 so as to inhibit the growth of cancer, so that The present invention extracts of *Artocarpus altilis* fruits, leaves, or stems, or the fractions as active ingredients a use of pharmaceutical composition for the treatment.

The present invention also provides a use of the extracts of *Artocarpus altilis* fruits, leaves, or stems as an active ingredient of health food composition for preventing and improving cancer thereof.

The present invention also provides a use of the fractions of *Artocarpus altilis* fruits, leaves, or stems extracts as an active ingredient of health food composition for preventing and improving cancer thereof.

The present invention extracts of *Artocarpus altilis* fruits, leaves, or stems, or the fractions thereof of the present invention could efficiently suppress the activity of STAT3 so as to inhibit the growth of cancer, so that The present invention extracts of *Artocarpus altilis* fruits, leaves, or stems, or the fractions as active ingredients a use of pharmaceutical composition for the treatment of cancer and health food composition for preventing cancer.

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1

Preparation of Extracts of *Artocarpus altilis* Fruits, Leaves, or Stems

<1-1> Preparation of Methanol Extract of *Artocarpus altilis* Fruits, Leaves, or Stems 1 kg of the dried *Artocarpus altilis* fruits, leaves, or stems (University of Ibadan, Ibadan, Nigeria) was pulverized, which was soaked in 4 l of methanol. The mixture stood at room temperature for 5 days. The crude extract was filtered and concentrated under reduced pressure. As a result, 60 g of methanol extract of *Artocarpus altilis* fruits, leaves, or stems was obtained.

<1-2> Preparation of Ethanol Extract of *Artocarpus altilis*

1 kg of the dried *Artocarpus altilis* fruits, leaves, or stems was pulverized, which was soaked in 4 l of ethanol. The mixture stood at room temperature for 5 days. The crude extract was filtered and concentrated under reduced pressure. As a result, 60 g of ethanol extract of *Artocarpus altilis* fruits, leaves, or stems was obtained.

<1-3> Preparation of Hot-Water Extract of *Artocarpus altilis*

1 kg of the dried *Artocarpus altilis* fruits, leaves, or stems was pulverized, which was soaked in 4 l of water. The mixture stood at 100° C. for 5 hours. The crude extract was filtered and concentrated under reduced pressure. As a result, 60 g of hot-water extract of *Artocarpus altilis* fruits, leaves, or stems was obtained.

Example 2

Preparation of Active Fractions of Extracts of *Artocarpus altilis* Fruits, Leaves, or Stems 10 g of the methanol extract of *Artocarpus altilis* fruits, leaves, or stems prepared in Example <1-1> was dissolved in 50 mL of methanol, which was absorbed by 500 g of C18. Serial elution was performed with 1 liter of each 50% methanol, 70% methanol, and 100% methanol in that order. As a result, 560 mg of active fraction was obtained from 70% methanol.

Experimental Example 1

Inhibitory Effect of the Extracts of *Artocarpus altilis* Fruits, Leaves, or Stems, and the Fractions Thereof on the Activity of STAT3 in a Rectal Cancer Cell Line Dual *luciferase* assay was performed to investigate the inhibitory effect of the extracts of *Artocarpus altilis* fruits, leaves, or stems, and the fractions thereof prepared in Example 1 and Example 2 on the activity of STAT3 in a rectal cancer cell line.

Particularly, a rectal cancer cell line (HCT116, ATCC, USA) was transfected with the plasmid increasing the expression of firefly *luciferase* in proportion to the activity of STAT3 and also transfected with the plasmid expressing *Renilla luciferase* regardless of the activity of STAT3. Those rectal cancer cells transfected with the said plasmids were detached by using 0.05% trypsin-EDTA and inoculated in each well of a 96-well test plate at the density of 10,000 cells/well. The cells were maintained in a medium supplemented with 10% FBS in a 37° C. 5% $CO_2$ incubator for 3 hours. Then, the cells were treated with 1% DMSO (control) or the extracts of *Artocarpus altilis* fruits, leaves, or stems, or the fractions thereof (dissolved in DMSO) at different concentrations (1/100 diluted). The activity of STAT3 was measured 12 or 24 hours later after firefly *luciferase* and *Renilla luciferase* specific substrates (Beetle luciferin and coelenterazine) were added stepwise. Luminous intensity displayed according to the decomposition of the substrate was measured by using Luminometer (Wallac 1420). The measured firefly *luciferase* activity reflected the activity of STAT3, which was in proportion to the activity, and non-specific cytotoxicity and internal deviation generated in each experiment were corrected by using *Renilla luciferase*.

In conclusion, the result of dual *luciferase* assay performed to investigate the inhibitory effect of the extracts of *Artocarpus altilis* fruits, leaves, or stems, or the fractions thereof on the activity of STAT3 in a rectal cancer cell line confirmed that the methanol extract of *Artocarpus altilis* fruits, leaves, or stems prepared in Example <1-1> suppressed the activity of STAT3 by 50% at the concentration of 50 ug/mL. And the fraction eluted from the extracts of *Artocarpus altilis* fruits, leaves, or stems by using 70% methanol suppressed the activity of STAT3 by 75% at the concentration of 50 ug/mL (FIG. 1).

Experimental Example 2

Inhibitory Effect of the Fractions of *Artocarpus altilis* Fruits, Leaves, or Stems, and the Fractions Thereof on the Activity of STAT3 in a Prostate Cancer Cell Line Western blotting was performed to investigate the inhibitory effect of the extracts of *Artocarpus altilis* fruits, leaves, or stems, and the fractions thereof prepared in Example 1 and Example 2 on the activity of STAT3 in a prostate cancer cell line.

Particularly, prostate cancer cells (DU145, ATCC, USA) were loaded in three 60 mm plates, 800,000 cells per each plate, followed by culture. The cells were maintained in a medium supplemented with 10% FBS in a 37° C. 5% $CO_2$ incubator. 24 hours later, the plates were treated respectively with 0.25% DMSO (control) and the fractions of *Artocarpus altilis* fruits, leaves, or stems at the concentrations of 20 ug/mL and 50 ug/mL, followed by further culture for 24 hours. Then, the medium was discarded from each plate and the cells were washed with PBS which was also discarded after washing. Ripa lysis buffer was added by 200 ul per plate, and then the cells attached on the plate were collected by using a scrapper. The collected lysed cells were transferred in a 1.5 ml tube, which was rotated in a rotator for 15 minutes at 4° C. Then, the tube was centrifuged at 13,000 rpm for about 15~30 minutes at 4° C. Upon completion of centrifugation, the supernatant was obtained from the tube and transferred in a new 1.5 ml tube. So, each lysate was prepared, and the protein in each lysate was measured. 800 ul of deionized water and 10 ul of each lysate were loaded in a 1.5 ml tube, to which 200 ul of Bradford assay reagent was added, followed by vortexing. The prepared lysate was loaded in three wells of a 96-well plate (200 ul/well). To quantify the protein in each lysate, $OD_{595}$ was measured by using an ELISA reader. Loading sample was prepared with the lysate, ripa lysis buffer, and 5× dye with assembling the protein to be equal amount for each sample. The prepared loading sample was boiled at 80° C. for 10 minutes, followed by incubation (inactivation). Acrylamide SDS gel was prepared to fit the size of the target protein and then the prepared loading sample and the marker were loaded on the gel. The loaded gel was transferred at 0.25 A for 2 hours to transfer the protein in the gel onto the membrane. Blocking of the protein transferred onto the membrane was performed by using skim milk for 1 hour. The primary antibody corresponding to the target protein was treated for 2 hours and then the secondary antibody (HRP) taking each primary antibody as its antigen was conjugated thereto for 1 hour. Then, HRP substrate was sprayed on the membrane. Chemoluminescence was measured by using LAS image analyzer (Fuji Co), which was photographed to investigate the expression of each protein.

As a result, the fractions of *Artocarpus altilis* fruits of the present invention suppressed the activity of STAT3 not only in the prostate cancer cell line DU145 but also in the STAT3 target proteins cycline D1, Bcl-xl, Bcl-2, VEGF, and survivin at the concentrations of 20 ug/mL and 50 ug/mL. Particularly, the active fractions of *Artocarpus altilis* suppressed the activity of STAT3 more strongly at the concentration of 50 ug/mL (FIG. 2).

Experimental Example 3

Inhibitory Effect of the Extracts of *Artocarpus altilis* Fruits, Leaves, or Stems, or the Fractions Thereof on Tumor Growth in a Prostate Cancer Cell Line Animal test was performed to investigate the inhibitory effect of the extracts of *Artocarpus altilis* fruits, leaves, or stems, or the fractions thereof prepared in Example 1 and Example 2 on tumor growth in a prostate cancer cell line.

Particularly, the human prostate cancer cell line DU-145 (adenocarcinoma; prostate cancer) was transplanted in BALB/C SPF nude mice at 5-6 weeks (female, Nara Biotech Co.) to construct the human tumor xenograft model. To transplant DU-145 cells in the nude mice, the cells were first counted and the density of the cells was adjusted to $3\times10^7$ cells/ml by using serum-free medium. The prepared cell culture solution was injected via hypodermic injection in the axilla between the right shoulder and the chest wall at the concentration of 0.3 ml ($9\times10^6$ cells/mouse). From the next day of cell transplantation (day 1), the test drug was administered. The tumor size of each animal was measured from three different sides of it by using a vernier caliper 5 times from day 14 to day 23, which was presented as the following formula: length×width×height/2. On the final day of experiment, the mice were sacrificed and the tumor of each mouse was extracted and weighed with a chemical balance. The fractions of the extracts of *Artocarpus altilis* fruits, leaves, or stems were dissolved in a mixed solution (dimethylacetamide 10%, Tween-80 10%, and distilled water containing 20% 2-hydroxypropyl β-cyclodextrin 80%) at the concentration of 3 mg/ml. This mixed solution was administered to the mice via peritoneal injection at the concentration of 10 ml/kg 17 times in total (day 1-day 22, 5 times a week).

Figure 3:
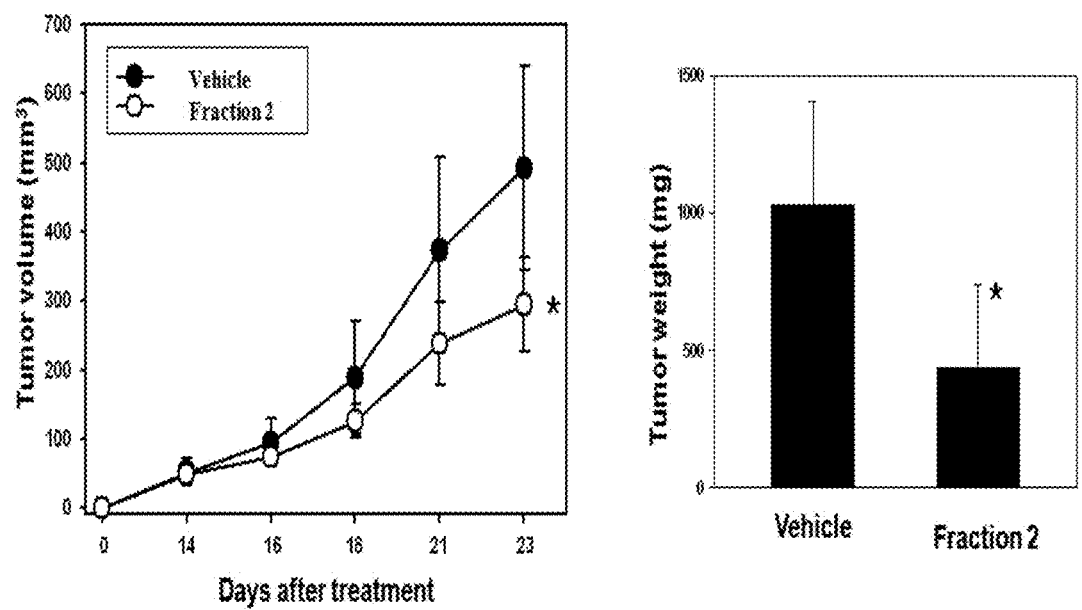
FIG. 3 is a diagram illustrating the inhibitory effect of the fractions of *Artocarpus altilis* fruits, leaves, or stems on prostate cancer.

As a result, compared with the solvent control, the inhibitory effect of the fractions of *Artocarpus altilis* fruits, leaves, or stems on tumor growth was significant in the group treated with 30 mg/kg of the fractions (35.0%, <0.05). When the tumor DU-145 was extracted and weighed, the result suggested that the fractions of the extracts of *Artocarpus altilis* fruits, leaves, or stems reduced the weight of the tumor significantly in the group treated with 30 mg/kg of the fractions (42.3%, <0.05). Therefore, it was confirmed that the fractions had the inhibitory effect on tumor growth in prostate cancer (FIG. 3).

Manufacturing Example 1

Preparation of Pharmaceutical Formulations

<1-1> Preparation of Powders

Methanol extract of *Artocarpus altilis* fruits, leaves, or stems of Example <1-1> 0.1 g

| | |
|---|---|
| Lactose | 1.5 g |
| Talc | 0.5 g |

Powders were prepared by mixing all the above components, which were filled in airtight packs according to the conventional method for preparing powders.

<1-2> Preparation of Tablets

Methanol extract of *Artocarpus altilis* fruits, leaves, or stems of Example <1-1> 0.1 g

| | |
|---|---|
| Lactose | 7.9 g |
| Crystalline cellulose | 1.5 g |
| Magnesium stearate | 0.5 g |

Tablets were prepared by mixing all the above components via direct tableting method.

<1-3> Preparation of Capsules

50% methanol extract of *Artocarpus altilis* fruits, leaves, or stems of Example 2 0.1 g

| | |
|---|---|
| Corn starch | 5 g |
| Carboxy cellulose | 4.9 g |

Capsules were prepared by mixing all the above components, which were filled in hard capsules according to the conventional method for preparing capsules.

<1-4> Preparation of Injectable Solutions

70% methanol extract of *Artocarpus altilis* fruits, leaves, or stems of Example 2 0.1 g

| | |
|---|---|
| Sterilized DW for injection | proper amount |
| pH regulator | proper amount |

Injectable solutions were prepared by mixing all the above components, which were filled in ampoules (2 ml/ampoule) according to the conventional method for preparing injectable solutions.

<1-5> Preparation of Liquid Formulations

100% methanol extract of *Artocarpus altilis* fruits, leaves, or stems of Example 2 0.1 g

| | |
|---|---|
| Isomerized sugar | 10 g |
| Mannitol | 5 g |
| Purified water | proper amount |

All the above components were dissolved in purified water. After adding lemon flavor, total volume was adjusted to be 100 ml by adding purified water. Liquid formulations were prepared by putting the mixture into brown bottles and sterilizing thereof by the conventional method for preparing liquid formulations.

Manufacturing Example 2

Preparation of Health Food

<2-1> Preparation of Flour Food 0.5~5.0 weight part of the hot-water extract of *Artocarpus altilis* fruits, leaves, or stems of Example <1-3> was added to flour. Health enhancing foods such as bread, cake, cookies, crackers and noodles were prepared with the flour mixture according to the conventional method.

<2-2> Preparation of Soups and Gravies 0.1~5.0 weight part of the hot-water extract of *Artocarpus altilis* fruits, leaves, or stems of Example <1-3> was added to soups and gravies. Health enhancing meat products, soups and gravies were prepared with this mixture by the conventional method.

<2-3> Preparation of Ground Beef

Health enhancing ground beef was prepared by mixing 10 weight part of the hot-water extract of *Artocarpus altilis* fruits, leaves, or stems of Example <1-3> with ground beef according to the conventional method.

<2-4> Preparation of Dairy Products

5~10 weight part of the hot-water extract of *Artocarpus altilis* fruits, leaves, or stems of Example <1-3> was added to milk. Health enhancing dairy products such as butter and ice cream were prepared with the milk mixture according to the conventional method.

<2-5> Preparation of Sun-Sik

Brown rice, barley, glutinous rice and Yulmu (Job's tears) were gelatinized according to the conventional method, dried and pulverized to obtain 60-mesh powders.

Black soybean, black sesame and wild sesame were steamed and dried according to the conventional method and pulverized to obtain 60-mesh powders.

The hot-water extract of *Artocarpus altilis* fruits, leaves, or stems of Example <1-3> was concentrated under reduced pressure, spray-dried and pulverized to obtain 60-mesh dry powders.

Sun-Sik was prepared by mixing the dry powders of the grains, seeds and the hot-water extract of *Artocarpus altilis* fruits, leaves, or stems of Example <1-3> according to the below ratio.

Grains (brown rice: 30 weight part, Yulmu: 15 weight part, barley: 20 weight part, glutinous rice: 10 weight part), Seeds (wild sesame: 7 weight part, black soybean: 8 weight part, black sesame: 7 weight part), Dry powders of the hot-water extract of *Artocarpus altilis* leaves or stems of Example <1-3>(1 weight part),

*Ganoderma lucidum* (0.5 weight part),

*Rehmannia glutinosa* (0.5 weight part)

<2-6> Preparation of Health Supplement Food

| | |
|---|---|
| Hot-water extract of *Artocarpus altilis* fruits, leaves, or stems of Example <1-3> | 100 mg |
| Vitamin complex | proper amount |
| Vitamin A acetate | 70 μg |
| Vitamin E | 1.0 mg |
| Vitamin B1 | 0.13 mg |
| Vitamin B2 | 0.15 mg |
| Vitamin B6 | 0.5 mg |
| Vitamin B12 | 0.2 μg |
| Vitamin C | 10 mg |
| Biotin | 10 μg |
| Nicotinic acid amide | 1.7 mg |
| Folic acid | 50 μg |
| Calcium pantothenate | 0.5 mg |
| Minerals | proper amount |
| Ferrous sulfate | 1.75 mg |
| Zinc oxide | 0.82 mg |
| Magnesium carbonate | 25.3 mg |
| Potassium phosphate monobasic | 15 mg |
| Potassium phosphate dibasic | 55 mg |
| Potassium citrate | 90 mg |
| Calcium carbonate | 100 mg |
| Magnesium chloride | 24.8 mg |

Vitamins and minerals were mixed according to the preferable composition rate for health food. However, the composition rate can be adjusted. The constituents were mixed according to the conventional method for preparing health food and then the composition for health food was prepared according to the conventional method.

Manufacturing Example 3

Preparation of Health Beverages

| | |
|---|---|
| Hot-water extract of *Artocarpus altilis* fruits, leaves, or stems of Example <1-3> | 100 mg |
| Citric acid | 100 mg |
| Oligosaccharide | 100 mg |
| Maesil (*Prunus mume*) Extract | 2 mg |
| Taurine | 100 mg |
| Purified water | up to 500 ml |

The above constituents were mixed according to the conventional method for preparing health beverages. The mixture was heated at 85° C. for 1 hour with stirring and then filtered. The filtrate was loaded in 1 l sterilized containers, which were sealed and sterilized again, stored in a refrigerator until they would be used for the preparation of a composition for health beverages.

The constituents appropriate for favorite beverages were mixed according to the preferred mixing ratio but the composition ratio can be adjusted according to regional and national preferences, etc.

INDUSTRIAL APPLICABILITY

As mentioned above, the present invention to can be effectively used a pharmaceutical composition for prevention and treatment of cancers selected from the group consisting of colorectal cancer, stomach cancer, prostate cancer, breast cancer, renal cancer, liver cancer, brain tumor, lung cancer, uterine cancer, colon cancer, bladder cancer, and pancreatic cancer, wherein the comprises the extracts of *Artocarpus altilis* fruits, leaves, or stems, or the fractions thereof as active ingredients.

What is claimed is:

1. A method for treating prostate cancer in a subject in need thereof comprising administering a pharmaceutically effective dose of an extract of *Artocarpus altilis* fruits to the subject.

2. The method of claim 1, wherein the extract is extracted by using water, $C_1$-$C_2$ lower alcohol, or a combination thereof, as a solvent.

3. The method of claim 2, wherein the $C_1$-$C_2$ lower alcohol is methanol or ethanol.

4. The method of claim 1, wherein the extract is characterized by suppressing the activity of STAT3 (signal transducers and activators of transcription 3).

* * * * *